(12) United States Patent
Smith et al.

(10) Patent No.: US 8,557,229 B2
(45) Date of Patent: Oct. 15, 2013

(54) HAIR REMOVAL METHOD AND HAIR REMOVAL KIT

(75) Inventors: Charles Robert Smith, Henley on Thames (GB); Stuart Andrew Hewlins, Woking (GB); Michael John Goffe, Egham (GB); Paul Jonathan Matts, Addlestone (GB); Paul James Smith, Whitton (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/070,837

(22) Filed: Mar. 24, 2011

(65) Prior Publication Data

US 2011/0232007 A1 Sep. 29, 2011

Related U.S. Application Data

(60) Provisional application No. 61/317,763, filed on Mar. 26, 2010.

(51) Int. Cl.
*A61K 8/02* (2006.01)

(52) U.S. Cl.
USPC .......... 424/70.1; 424/420; 424/443; 424/401; 424/70.11; 8/94.16; 8/161

(58) Field of Classification Search
USPC .................. 424/401, 420; 8/94.16, 161
See application file for complete search history.

(56) References Cited

U.S. PATENT DOCUMENTS

| | | | |
|---|---|---|---|
| 2,202,829 A | 6/1940 | Buff | |
| 3,194,736 A | 7/1965 | Ernest | |
| 3,981,681 A | 9/1976 | de la Guardia | |
| 4,121,904 A | 10/1978 | Schamper | |
| 4,177,260 A | 12/1979 | Wajaroff | |
| 4,282,877 A | 8/1981 | Mathews | |
| 4,424,205 A | 1/1984 | LaHann | |
| 4,546,112 A | 10/1985 | LaHann | |
| 4,830,633 A * | 5/1989 | Hori et al. .................. 8/160 |
| 5,026,542 A | 6/1991 | Baines | |
| 5,220,064 A | 6/1993 | Johnson | |
| 5,645,825 A | 7/1997 | Hillebrand | |
| 5,648,394 A | 7/1997 | Boxall | |
| 5,725,847 A | 3/1998 | De La Mettrie | |
| 6,203,784 B1 | 3/2001 | Martin | |
| 6,306,380 B1 | 10/2001 | Desmots | |
| 6,479,043 B1 | 11/2002 | Tietjen | |
| 2002/0146380 A1 | 10/2002 | Nambu | |
| 2004/0180014 A1 | 9/2004 | Gupta | |
| 2004/0219118 A1* | 11/2004 | Slavtcheff et al. ........... 424/70.1 |
| 2005/0124984 A1 | 6/2005 | Wagnieres | |
| 2006/0002878 A1 | 1/2006 | Acher | |
| 2009/0117068 A1 | 5/2009 | Ellis | |
| 2010/0083443 A1 | 4/2010 | Tindal | |

FOREIGN PATENT DOCUMENTS

| | | |
|---|---|---|
| BE | 626897 | 1/1963 |
| CA | 2354829 | 2/2003 |
| EP | 0085894 | 3/1984 |
| EP | 0095916 | 8/1984 |
| EP | 0089710 | 7/1985 |
| EP | 0161681 | 4/1987 |
| EP | 1312353 | 5/2003 |
| EP | 1902752 | 3/2008 |
| FR | 2347040 | 11/1977 |
| GB | 1264319 | 2/1972 |
| GB | 2306323 | 1/1998 |
| WO | WO9110421 | 7/1991 |
| WO | WO9308791 | 5/1993 |
| WO | WO9421216 | 9/1994 |
| WO | WO9902125 | 1/1999 |
| WO | WO2004096164 | 11/2004 |
| WO | WO2007031793 | 6/2008 |
| WO | WO2008110745 A3 | 1/2009 |
| WO | WO2009042026 | 4/2009 |

OTHER PUBLICATIONS

Chemical Abstracts, vol. 81, No. 17, Oct. 28, 1974, "Synthesis of Homovanillic Acid Derivatives of Capsaicin-Like Effect", P. Hegyes, et al., 7 pages.
Arzneimittel-Forschung, vol. 25, No. 12, Dec. 1975, "Sensory Effects of Capsaicin Congeners—Relationship Between Chemical Structure and Pain-Producing Potency of Pungent Agents", 5 pages.

* cited by examiner

*Primary Examiner* — Rebecca Prouty
*Assistant Examiner* — Danielle Sullivan
(74) *Attorney, Agent, or Firm* — S. Robert Chuey

(57) ABSTRACT

A method of removing hair from skin, preferably facial skin, is provided, comprising the steps of:
(a) applying a hydrophobic protective composition to an area of skin, preferably facial skin, on which unwanted hair is growing, the hydrophobic protective composition being capable of reducing the penetration of thioglycolic acid by at least 45%, as measured using the Franz Cell Method;
(b) applying a depilatory composition to the area of skin to which the hydrophobic protective composition has been applied, the depilatory composition comprising a keratin reducing agent.

8 Claims, 2 Drawing Sheets

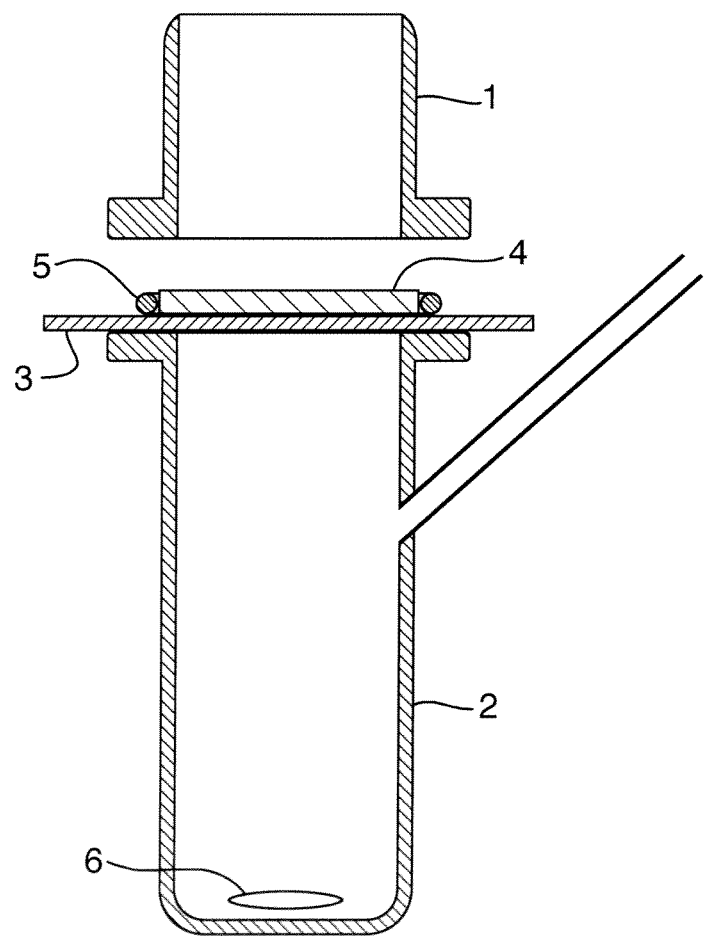

HAIR REMOVAL METHOD AND HAIR REMOVAL KIT

CROSS REFERENCE TO RELATED APPLICATION

This application claims the benefit of U.S. Provisional Application No. 61/317,763, filed 26 Mar. 2010.

FIELD OF THE INVENTION

The present invention relates to a depilatory method and kit.

BACKGROUND OF THE INVENTION

Depilatory compositions are cosmetic hair removal formulations. They comprise keratin reducing agents, which attack the disulphide bonds in hair to weaken it, such that subsequent gentle scraping and/or wiping completes severance of the hair from the skin and effects hair removal. Commercially, the most common keratin reducing agents are thioglycolates, which are typically formulated at high pH. An unwanted side effect of chemical depilation is that the depilatory composition comes into contact with and must have a relatively long residence time on skin to achieve effective hair removal and this long residence time combined with the alkaline conditions needed for effective hair removal may give rise to skin irritation.

The above problem has been recognized in the art. Reference is made to US 2004/0219118, which discloses treatment with a "lipophilic" material before application of a thioglycolate-based reactive depilatory composition. Lipophilic materials exemplified in this patent application are oils, such as mineral oil. As shown hereinbelow, the present applicants have tested a range of lipophilic materials to determine their ability to prevent thioglycolate penetration and, thereby, their ability to reduce or prevent skin irritation Applicants have surprisingly found that oils, such as mineral oil, have no or a low ability to prevent thioglycolate penetration to the skin. There thus exists a need to develop a pre-treatment composition which better reduces skin irritation.

SUMMARY OF THE INVENTION

According to a first aspect of the invention, a method of removing hair from skin, preferably facial skin, is provided, comprising the steps of:
(a) applying a hydrophobic protective composition to an area of skin, preferably facial skin, on which unwanted hair is growing, the hydrophobic protective composition being capable of reducing the penetration of thioglycolic acid by at least 45%, as measured using the Franz Cell Method;
(b) applying a depilatory composition to the area of skin to which the hydrophobic protective composition has been applied, the depilatory composition comprising a keratin reducing agent.

According to a second aspect of the invention, a depilatory kit is provided comprising:
(a) a hydrophobic protective composition, the hydrophobic protective composition, the hydrophobic protective composition being capable of reducing the penetration of thioglycolic acid by at least 45%, as measured using the Franz Cell Method;
(b) a depilatory composition comprising an effective amount of a keratin reducing agent.

BRIEF DESCRIPTION OF THE DRAWINGS

FIG. 2 is a schematic view of a Franz Cell apparatus.

DETAILED DESCRIPTION OF THE INVENTION

Figure 1:
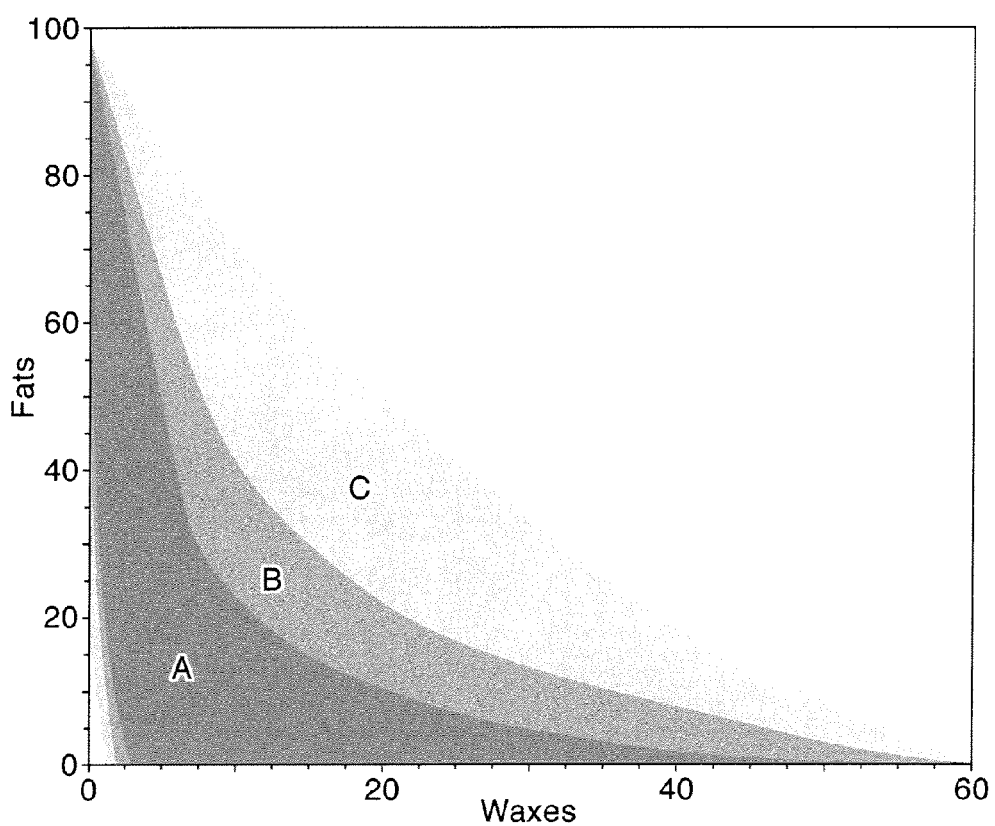
FIG. 1 is a graph teaching how to mix waxes and triglycerides according to the invention

Applicants have developed a test method to establish the penetration of thioglycolate to the skin. This test, referred to herein as the "Franz Cell Method", is defined hereinbelow. Surprisingly, applicants have established that hydrophobic protective compositions may be devised which reduce penetration of thioglycolic acid according to the Franz Cell Method by over 45%. A reduction of thioglycolic acid penetration of 45% or more may be shown to correlate to a significant and user-noticeable reduction in irritation.

In order to achieve the above reduction in penetration, applicants have established that the hydrophobic protective composition may comprise defined amounts of one or more hydrophobic components which are solid at 25° C. The solid hydrophobic component(s) may comprise, but are not limited to, wax, triglyceride, and mixtures thereof. Without wishing to be bound by theory, applicants believe that the presence of defined amounts of one or more solid hydrophobic components may militate against the tendency otherwise exhibited by oils to ball up and reduce their surface area on skin when in contact with a mainly aqueous depilatory composition and therefore disrupt the barrier. The solid hydrophobic component(s) may also ensure that a thin and continuous film of the hydrophobic protective composition can be evenly distributed across the skin, even at a low dosage per unit area. In addition, the solid hydrophobic component(s) may enable the formation of a film across the skin that is chemically resistant to ingress from the thioglycolate (or other reducing) actives, therefore physically reducing the ability for the harsh chemistry to come into contact with the skin. This reduction in contact means that the stratum corneum may be maintained in a better state than if no barrier were present with correspondingly reduced signs of irritation, such as erythema, tingling and stinging.

At the same time as reducing contact between the depilatory active ingredient and the skin, the present hydrophobic protective compositions are observed not noticeably to reduce the ability of the depilatory composition to attack and degrade the unwanted hair growing on that skin. Why this should be is not understood, but it may simply be due to the fact that less of the hydrophobic protective composition adheres to the hairs than to the skin.

As used herein, the term "wax" includes, but is not limited to, any hydrophobic material that is:
  Solid at 25° C.
  practically insoluble in water according to the United States' Pharmacopeia (USP) definition in 31/NF 26 Vol. 2 General Notices, Page Xvii. (which, according to that definition, means that more than 10,000 parts of water are needed to dissolve 1 part solute);
  has an onset temperature measured according to the DSC Method, defined hereinbelow, which is 10° C. or greater; and
  comprises lipids, silicones or mixtures thereof.

As used herein, the term "triglyceride" refers to a material having the following formula:

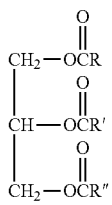

wherein R, R' and R" may be the same as or different from one or both of the others and wherein each of R, R' and R" is a fatty acid and wherein the or each triglyceride is solid at 25° C.

Suitable waxes may comprise natural wax, synthetic wax, silicone wax, or mixtures thereof.

Non-limiting examples of suitable natural waxes include *Abies* Alba Leaf Wax, *Acacia Dealbata* Leaf Wax, *Acacia Farnesiana* Flower Wax, Beeswax, Ceresin, Cetyl Esters, *Cistus Labdaniferus* Flower Wax, *Aurantium Amara* (Bitter Orange) Flower Wax, *Aurantium Dulcis* (Orange) Peel Wax, *Copernicia Cerifera* (Carnauba) Wax, *Eclipta Prostrata* Wax, *Euphorbia Cerifera* (Candelilla) Wax, *Helichrysum Angustifolium* Wax, *Jasminum Officinale* (Jasmine) Flower Wax, *Jasminum Sambac* (Jasmine) Flower Wax, Jojoba Esters, Jojoba Wax, Lanolin Wax, *Lavandula Angustifolia* (Lavender) Flower Wax, *Lawsonia Inermis* Wax, Mink Wax, Montan Acid Wax, Montan Wax, *Myrica Cerifera* (Bayberry) Fruit Wax, *Ocimum Tenuiflorum* Wax, Olive Wax, *Oryza Sativa* (Rice) Bran Wax, Ouricury Wax, Palm Kernel Wax, *Persea Gratissima* (Avocado) Wax, *Pistacia Lentiscus* Leaf Wax, *Polianthes Tuberosa* Flower Wax, *Pyrus Malus* (Apple) Peel Wax, *Ribes Nigrum* (Black Currant) Wax, *Rosa Centifolia* Flower Wax, *Salvia Sclarea* (Clary) Wax, Shellac Wax, *Simmondsia Chinensis* (Jojoba) Butter, Soft Olive Wax, Spent Grain Wax, *Stipa Tenacissima* Wax, Sunflower Seed Wax, Vegetable Wax, *Vitis Vinifera* (Grape) Leaf Wax and mixtures thereof.

Non-limiting examples of suitable synthetic waxes include Hydrogenated Japan Wax, Hydrogenated Jojoba Oil, Hydrogenated Jojoba Wax, Hydrogenated Microcrystalline Wax, Hydrogenated Rice Bran Wax, Hydrolyzed Beeswax, Microcrystalline Wax, Oxidized Beeswax, Oxidized Microcrystalline Wax, Ozokerite, Paraffin, PEG-6 Beeswax, PEG-8 Beeswax, PE G-12 Beeswax, PEG-20 Beeswax, PEG-12 Carnauba, Potassium Oxidized Microcrystalline Wax, Sulfurized Jojoba Oil, Synthetic Beeswax, Synthetic Candelilla Wax, Synthetic Carnauba, Synthetic Japan Wax, Synthetic Jojoba Oil, Synthetic Wax and mixtures thereof.

Non-limiting examples of suitable silicone waxes include DC2503 Cosmetic Wax, DC580 wax, DC AMS-C30 Cosmetic Wax, C30-45 Alkyl Methicone, DC Silkywax 10, Hexamethyldisiloxane, DC ST-Wax 30, C30-45 Alkyldimethylsilyl Polypropylsilsesquioxane, DC SW-8005 resin wax, C26-28 Alkyl Dimethicone, C26-28 Alkyl Methicone, Polyphenylsilsesquioxane and mixtures thereof.

Advantageously, the wax comprises beeswax, carnauba wax, candelilla wax, jojoba wax, paraffin wax, microcrystalline wax, ozokerite, arachidyl behenate, or mixtures thereof.

If the hydrophobic protective composition used in the method and comprised within the kit according to the invention comprises wax, then the hydrophobic composition should comprise from 1% to 60%, preferably from 2% to 24% and, more preferably, 3% to 15% wax by weight of the hydrophobic protective composition. At wax levels above 60% by weight, the hydrophobic protective composition may become difficult to handle and apply and may also be brittle, crack and fall off the skin. At wax levels below 1% the benefits of the invention may not be achieved, unless triglycerides are also present. In such a case, it is possible to operate with as little as 0.5% wax by weight of the hydrophobic protective composition, as discussed below.

In relation to the triglycerides, suitable oils from which triglycerides may be formed from include, but are not limited to, the oils listed herein. Suitable fatty acids for formation of the triglycerides include, but are not limited to, Myristoleic acid, Palmitoleic acid, Sapienic acid, Oleic acid, Linoleic acid, α-Linolenic acid, Arachidonic acid, Eicosapentaenoic acid, Docosahexaenoic acid, Lauric acid ($C_{12}$), Myristic acid ($C_{14}$), Palmitic acid ($C_{16}$), Stearic acid ($C_{18}$), Arachidic acid ($C_{20}$) and mixtures thereof.

Specific sources of triglycerides suitable for inclusion in the protective composition include include Butter, Shea Butter, *Butyrospermum Parkii, Theobroma Cacao* (Cocoa) Seed Butter, Cocoa Butter, Hydrogenated Shea Butter, Hydrogenated Cocoa Butter, *Irvingia Gabonensis* Kernel Butter, Tallow, Lard, *Mangifera Indica* (Mango) Seed Butter, Kokum Butter and mixtures thereof.

If the hydrophobic protective composition used in the method and comprised within the kit according to the invention comprises triglyceride(s), then the hydrophobic composition should comprise 20% or more, preferably 50% or more and more preferably from 75% to 99% of triglyceride(s) by weight of the protective composition. At triglyceride levels below 20%, the benefits of the invention may not be achieved, unless waxes are also present. In the case in which wax is mixed with the triglyceride, then, as discussed below, it is possible to operate with less than 20% triglyceride by weight of the hydrophobic protective composition.

Advantageously, the or each triglyceride has an onset temperature of less than 65° C. as measured by Differential Scanning Calorimetry, using the method defined hereinbelow. If the composition comprises triglycerides having an onset temperature outside this range, then it may become increasingly difficult to apply and may even crack and fall off in use.

The hydrophobic protective composition may comprise homogenous mixtures of waxes, triglycerides and other solid components in order to achieve a reduction in penetration of at least 45% using the Franz Cell Method. A reduction in penetration of at least 45% using the Franz Cell Method may be achieved via a combination of wax, in the above-defined amounts, with triglyceride, in the above-defined amounts. More broadly, a reduction in penetration of at least 45% using the Franz Cell Method may be achieved by operating in one of the shaded regions shown in FIG. 1, in which the order of preference for operation is region A being preferred, region B being less preferred and region C being less preferred still. Very specifically, when operating with a composition comprising from 0.5% to 3% wax by weight of the hydrophobic protective composition, combination with triglyceride is desirable, particularly in a weight ratio range of wax:triglyceride of 1:8 to 1:25, preferably 1:10 to 1:20, more preferably 1:15 to 1:20. The combination of the waxes and triglycerides may improve barrier-formation on skin, thereby reducing barrier mobility and therefore the ability for the actives within the depilatory composition to penetrate and cause damage to the skin.

The hydrophobic protective composition used in the method and comprised within the kit according to the invention may comprise oil. The oil may be selected from natural oil, synthetic oil, silicone oil and mixtures thereof.

Non-limiting examples of suitable natural oils include Acetylated Castor Oil, Acetylated Hydrogenated Castor Oil, *Actinidia Chinensis* (Kiwi), Seed Oil, *Adansonia Digitata* Oil, *Aleurites Moluccana* Seed Oil, *Anacardium Occidentale*

(Cashew) Seed Oil, *Arachis Hypogaea* (Peanut) Oil, *Arctium Lappa* Seed Oil, *Argania Spinosa* Kernel Oil, *Argemone Mexicana* Oil, *Avena Sativa* (Oat) Kernel Oil, *Bertholletia Excelsa* Seed Oil, *Borago Officinalis* Seed Oil, *Brassica Campestris* (Rapeseed) Seed Oil, *Calophyllum Tacamahaca* Seed Oil, *Camellia Japonica* Seed Oil, *Camellia Kissi* Seed Oil, *Camellia Oleifera* Seed Oil, Canola Oil, Caprylic/Capric/Lauric Triglyceride, Caprylic/Capric/Linoleic Triglyceride, Caprylic/Capric/Myristic/Stearic Triglyceride, Caprylic/Capric/Stearic Triglyceride, Caprylic/Capric Triglyceride, *Carthamus Tinctorius* (Hybrid Safflower) Seed Oil, *Carthamus Tinctorius* (Safflower) Seed Oil, *Carum Carvi* (Caraway) Seed Oil, *Carya Illinoensis* (Pecan) Seed Oil, Castor Oil Benzoate, *Chenopodium Quinoa* Seed Oil, *Cibotium Barometz* Oil, *Citrullus Vulgaris* (Watermelon) Seed Oil, *Cocos Nucifera* (Coconut) Oil, Cod Liver Oil, *Coffea Arabica* (Coffee) Seed Oil, *Coix Lacryma-Jobi* (Job's Tears) Seed Oil, *Corylus Americana* (Hazel) Seed Oil, *Corylus Avellana* (Hazel) Seed Oil, *Cucumis Sativus* (Cucumber) Oil, *Cucurbita Pepo* (Pumpkin) Seed Oil, *Daucus Carota Sativa* (Carrot) Seed Oil, *Elaeis Guineensis* (Palm) Kernel Oil, *Elaeis Guineensis* (Palm) Oil, *Gossypium* (Cotton) Seed Oil, *Helianthus Annuus* (Hybrid Sunflower) Oil, *Helianthus Annuus* (Sunflower) Seed Oil, *Hippophae Rhamnoides* Oil, Human Placental Lipids, Hydrogenated Canola Oil, Hydrogenated Castor Oil, Hydrogenated Castor Oil Laurate, Hydrogenated Castor Oil Triisostearate, Hydrogenated Coconut Oil, Hydrogenated Cottonseed Oil, Hydrogenated C12-18 Triglycerides, Hydrogenated Fish Oil, Hydrogenated Lard, Hydrogenated Menhaden Oil, Hydrogenated Mink Oil, Hydrogenated Olive Oil, Hydrogenated Orange Roughy Oil, Hydrogenated Palm Kernel Oil, Hydrogenated Palm Oil, Hydrogenated Peanut Oil, Hydrogenated Rapeseed Oil, Hydrogenated Shark Liver Oil, Hydrogenated Soybean Oil, Hydrogenated Sunflower Seed Oil, Hydrogenated Tallow, Hydrogenated Vegetable Oil, Isatis Tinctoria Seed Oil, *Juglans Regia* (Walnut) Seed Oil, Lauric/Palmitic/Oleic Triglyceride, *Umnanthes Alba* (Meadowfoam) Seed Oil, *Unum Usitatissimum* (Linseed) Seed Oil, *Lupinus Albus* Seed Oil, *Macadamia Integrifolia* Seed Oil, *Macadamia Ternifolia* Seed Oil, Maleated Soybean Oil, *Mangifera Indica* (Mango) Seed Oil, Marmot Oil, *Melaleuca Alternifolia* (Tea Tree) Leaf Oil, *Melia Azadirachta* Seed Oil, *Melissa Officina lis* (Balm Mint) Seed Oil, Menhaden Oil, Mink Oil, *Moringa pterygosperma* Seed Oil, *Mortierella* Oil, Neatsfoot Oil, *Nelumbium Speciosum* Flower Oil, *Nigella Sativa* Seed Oil, *Oenothera Biennis* (Evening Primrose) Oil, *Olea Europaea* (Olive) Fruit Oil, *Olea Europaea* (Olive) Husk Oil, Orange Roughy Oil, *Orbignya Cohune* Seed Oil, *Orbignya Oleifera* Seed Oil, *Oryza Sativa* (Rice) Bran Oil, *Oryza Sativa* (Rice) Germ Oil, Ostrich Oil, Oxidized Corn Oil, Oxidized Hazel Seed Oil, *Papaver Orientale* (Poppy) Seed Oil, *Passiflora Edulis* Seed Oil, *Persea Gratissima* (Avocado) Oil, *Pistacia Vera* Seed Oil, Placental Lipids, *Prunus Amygdalus Amara* (Bitter Almond) Kernel Oil, *Prunus Amygdalus* Dulcis (Sweet Almond) Oil, *Prunus Armeniaca* (Apricot) Kernel Oil, *Prunus Avium* (Sweet Cherry) Seed Oil, *Prunus Cerasus* (Bitter Cherry) Seed Oil, *Prunus Persica* (Peach) Kernel Oil, *Pyrus Malus* (Apple) Oil, *Ribes Nigrum* (Black Currant) Seed Oil, *Ricinus Communis* (Castor) Seed Oil, *Rosa Canina* Fruit Oil, *Rosa Moschata* Seed Oil, Salmon Oil, *Salvia Hispanica* Seed Oil, *Santalum Album* (Sandalwood) Seed Oil, *Sesamum Indicum* (Sesame) Seed Oil, Shark Liver Oil, *Solanum Lycopersicum* (Tomato) Seed Oil, Soybean Lipid, Sphingolipids, *Taraktogenos Kurzii* Seed Oil, *Telphairia Pedata* Oil, Vegetable Oil, *Vitis Vinifera* (Grape) Seed Oil, *Zea Mays* (Corn) Germ Oil, *Zea Mays* (Corn) Oil and mixtures thereof.

Non-limiting examples of suitable synthetic oils include mineral oil, isopropyl pamitate, isopropyl stearate, isohexadecane, isododecane, polyglyceryl triisostearate and mixtures thereof. Non-limiting examples of suitable silicone oils include dimethicones (including partial esters of dimethicones and fatty acids derived from natural/synthetic oils), cyclomethicones, polydimethylsiloxanes (e.g. DC200 from Dow Corning), phenyl trimethicones, trimethyl pentaphenyl trisiloxane, dimethicone copolyols and mixtures thereof.

The hydrophobic protective composition used in the method and comprised within the kit according to the invention may comprise skin active agents such as, but not limited to oil soluble vitamins, such as vitamin E derivatives, including vitamin E acetate and tocopherol nicotinate; oil-soluble vitamin A derivatives, such as retinyl palmitate; lanolin; ceramides; sterols and sterol esters; salicylic acid; camphor; eucalyptol; essential oils and mixtures thereof. These materials may also fall under the definition of "wax" or "triglyceride" as used herein and, in such a case, should be included as a wax or triglyceride for the purposes of determining the proportions of these materials.

The hydrophobic protective composition used in the method and comprised within the kit according to the invention may include further ingredients such as, but not limited to metal oxides, organic and inorganic dyes, lakes, micas, flavourings, perfumes and mixtures thereof.

Any depilatory composition comprising a suitable keratin reducing agent may be used in the present method and included in the present kit. Non-limiting examples of suitable keratin reducing agents include: sulphide salts such as $Li_2S$, $Na_2S$, $K_2S$, MgS, CaS, SrS or BaS, hydrogen sulphide salts such as NaSH or KSH; thioglycol; thioglycerol; thioglycolamide; thioglycolhydrazide; thioglycolic acid; thioglycolate salts (such as potassium thioglycolate, calcium thioglycolate, ammonium thioglycolate, diammonium dithioglycolate, glyceryl monothioglycolate, or monoethanolamine thioglycolate); thiosalicylic acid; thiomalic acid; ammonium thiolactate; monoethanolamine thiolactate; dithioerythritol; 2-mercaptopropionic acid; 1,3-dithiopropanol; glutathione; dithiothreitol; cysteine; homocysteine; N-acetyl-L-cysteine and cysteamine. Advantageously, the keratin reducing agent is comprised within the depilatory composition in an amount from 0.3% to 20%, preferably from 0.8% to 15%, more preferably from 1% to 10% by weight of the depilatory composition.

Advantageously, the depilatory composition may comprise at least one thioglycolate salt or thioglycollic acid acting as a hair removal agent when the depilatory composition is applied to unwanted hair. Preferably, the depilatory composition comprises sodium, potassium, magnesium, calcium, beryllium, strontium, zinc, monoethanolamine, ammonium, tetralkylammonium, imidazolium, pyridinium, phosphonium or glyceryl thioglycolate salts, or mixtures thereof, which may include dianion forms of thioglycolate. More preferably, the depilatory composition comprises at least one of sodium, potassium, magnesium or calcium thioglycolate, or mixtures thereof. Even more preferably the depilatory composition comprises potassium or calcium thioglycolate, or mixtures thereof.

The pH of the depilatory composition may advantageously be in the range of from 6 to 13.8, preferably from greater than 7 to 13, more preferably from 9 to 12.9, even more preferably from 10 to 12.8, even more preferably still from 12 to 12.75 and yet more preferably from 12.3 to 12.6 to improve the efficacy of the active ingredient. The depilatory composition may, in a preferred embodiment, comprise at least one base to control the pH. Preferably, the depilatory composition comprises potassium hydroxide; sodium hydroxide; lithium hydroxide; calcium hydroxide; barium hydroxide; caesium hydroxide; sodium hydroxide; ammonium hydroxide; strontium hydroxide; rubidium hydroxide; magnesium hydroxide; zinc hydroxide; sodium carbonate; pyridine; ammonia; alkanolamides (including monoethanolamine, diethanolamine, triethanolamine), phosphates (including tetrasodium phosphate), arginine or mixtures thereof. More preferably, the depilatory composition comprises at least one buffering base, even more preferably the depilatory composition comprises calcium hydroxide, magnesium hydroxide; barium hydroxide; strontium hydroxide; zinc hydroxide; arginine or mixtures thereof. Still more preferably the depilatory composition comprises calcium hydroxide; magnesium hydroxide, zinc hydroxide, sodium hydroxide, potassium hydroxide or mixtures thereof. Even more preferably still, the depilatory composition comprises calcium hydroxide, sodium hydroxide or mixtures thereof.

In an advantageous embodiment, the base is present at a concentration of from 0.1% to 10.0%, more preferably from 0.5% to 8.0% and even more preferably from 1.0% to 5.0%, by weight of the depilatory composition.

The concentration of water in the depilatory composition is preferably at least 40%, more preferably from 50% to 98%, even more preferably from 60% to 95% and even more preferably still from 70% to 90%, by weight of the depilatory composition.

The depilatory composition may optionally comprise a thickening agent. A representative but not exhaustive list can be found in "The Encyclopaedia of Polymers and Thickeners for Cosmetics" compiled and edited by Robert Y. Lochhead, PhD and William R. Fron, Department of Polymer Science, University of Southern Mississippi. Exemplary classes of thickening agents include gums, carbomers, polymers and copolymers of acrylic acid, associated thickeners, layered silicates/clays and natural polymers (including polysaccharides). One or more thickening agents may be included in the aqueous depilatory composition. The thickening agent may be present at a level of from about 0.01% to about 20%, preferably from about 0.1% to about 10% by weight of the depilatory composition.

The depilatory composition may also include other skin care ingredients such as conditioning agents selected from the group consisting of humectants, moisturizers, or skin conditioners (including mineral oil; almond oil; chamomile oil; jojoba oil; avocado oil; shea butter, niacinamide and glycerine); skin rejuvenation compositions (for example targeted for fine lines, wrinkles and uneven skin tone, including retinoids), cosmetic compositions; anti-inflammatory agents (including corticosteroids); anti-oxidants (including flavonoids) radical scavengers; sunscreen agents; skin cooling or warming agents and the like. The depilatory composition may comprise one or more skin care ingredients present in an amount of from about 0.001% to about 10%, more preferably from about 0.01% to about 7%, and even more preferably from about 0.025% to about 5%, by weight of the depilatory composition.

An accelerant may be employed in the depilatory composition. This optional component accelerates the rate of depilatory action of the depilatory agent. Suitable accelerants include, but are not limited to, urea; thiourea; dimethyl isosorbide; arginine salts; ethoxydiglycol; propylene glycol and methylpropyldiol. The accelerant may be present in a concentration range of from 0.5% to 10%, more preferably from 2% to 8% and even more preferably from 2% to 5% by weight of the depilatory composition.

The depilatory composition may further comprise components known, conventionally used, or otherwise effective for use in cosmetic compositions, such as dyes; pigments (including ultra marines and talc); anionic, cationic, non-ionic and/or amphoteric or zwitterionic surfactants, polymers (including hydrophobically modified polymers); dispersing agents; solvents; lubricants; fragrances; preservatives; chelants, proteins and derivatives thereof, plant materials (e.g. aloe, chamomile and henna extracts); silicones (volatile or non-volatile, modified or non-modified); film-forming agents; film forming promoters and mixtures thereof.

The depilatory composition may be formulated in any common delivery form, such as a cream or lotion. Alternatively, it may be delivered on a substrate, such as a thin film of depilatory composition coated onto the substrate. The substrate may be configured in any suitable form, such as a strip, mask or patch.

In addition to the hydrophobic protective composition and the depilatory composition, the kit according to the second aspect of the invention may comprise one or more of:
  (a) A make-up removal composition and/or a make-up removal wipe;
  (b) Means for removal of the hydrophobic protective composition and the depilatory composition following use, which means may comprise one or more of a tool, such as a scraper or a spatula; or a wipe;
  (c) A post-treatment composition skin care composition to be applied to the area of skin from which hair has been removed. Such a post-treatment skin care composition may comprise ingredients to promote skin conditioning; moisturizers, skin rejuvenation compositions (targeted for fine lines, wrinkles and uneven skin tone, for example), cosmetic compositions (e.g., foundation, rouge), sunscreens and the like. The post-treatment skin care composition may be leave-on or a rinse-off composition.
  (d) Instructions regarding how to use the various elements of the kit, which instructions may comprise one or more elements of the method as defined herein.

Prior to applying the method or using the kit according to the present invention, a user should advantageously remove all make-up from the skin, to ensure good adherence and effective application of both the hydrophobic protective composition and the depilatory composition.

The method according to the first aspect of the invention comprises the step of applying the above-defined hydrophobic protective composition to an area of skin on which unwanted hair is growing. The area of skin may be located on any part of the human body, but is preferably on the face, more preferably on an area of skin adjacent to the vermillion lip and more preferably still on an area above the upper vermillion lip.

Advantageously, the hydrophobic protective composition is not just applied to the area to be depilated, but also to an immediately juxtaposing area thereabout (that is, the hydrophobic protective composition is applied to an area of skin which is greater than just the area which is to be depilated).

Advantageously, the user will apply from 0.3-2 mg of hydrophobic protective composition per square centimetre of skin, preferably from 0.4-1 $mg/cm^2$, more preferably from 0.4 to 0.7 $mg/cm^2$.

Following application, the hydrophobic protective composition is advantageously massaged into the skin. Preferably, massaging is effected for at least 10 seconds, and, more preferably, massaging is effected as a circular motion. Without wishing to be bound by theory, it is believed that the hydrophobic protective composition may trap hair within it thereby shielding it from the to-be-applied depilatory composition; massaging may help to release the hairs from the skin and ensure improved access thereto by the depilatory composition.

The method according to the first aspect of the invention comprises the subsequent step of applying the above-defined depilatory composition to an area of skin on which unwanted hair is growing and to which hydrophobic protective composition has already been applied. Advantageously, the user will apply a layer of depilatory composition which is from 0.1 mm to 5 mm, preferably from 0.3 to 3 mm, more preferably from 0.5 to 2 mm in thickness.

Subsequently, according to the method of the first aspect of the invention, the depilatory composition is advantageously left in place for at least 1 minute, preferably from 1 to 10 minutes, more preferably from 3 to 10 minutes, depending on the thickness of the hair and the hair removal efficacy of the depilatory composition (which, in turn, is dependent upon the concentration of keratin reducing agent in the depilatory composition).

Subsequently, according to the method of the first aspect of the invention, the hydrophobic protective composition and the depilatory composition are advantageously removed. This may be achieved using one or more of a cotton wool ball, pad or wand, a tissue, a cloth, or a tool, such as a spatula or a scraper. Advantageously, the skin from which hair has been removed is then rinsed with water.

In an advantageous subsequent step, a post-treatment skin care composition may be applied to the area of skin from which hair has been removed. Such a post-treatment skin care composition may comprise ingredients to promote skin conditioning; moisturizers, skin rejuvenation compositions (targeted for fine lines, wrinkles and uneven skin tone, for example), cosmetic compositions (e.g., foundation, rouge), sunscreens and the like. The post-treatment skin care composition may be leave-on or a rinse-off composition.

Differential Scanning Calorimetry (DSC) Melting Method

This method is the American Oil Chemists' Society Method Cj 1-94, as reapproved in 2009 and it determines the "onset temperature" (that is the temperature of onset of melting) of oils and fats by differential scanning calorimetry (DSC).
Apparatus
1. Aluminum capsules.
2. DSC instrument, capable of holding temperature at −60° C. and achieving a temperature of 80° C.
Regents
1. Indium, powder—60 mesh, 99.999%, such as Aldrich Chemical Co., Milwaukee, Wis. 53233, or equivalent.
2. n-Decane, 99+%, such as Aldrich Chemical Co., Milwaukee, Wis. 53233, or equivalent.
3. Methyl stearate, 99%, such as Aldrich Chemical Co., Milwaukee, Wis. 53233, or equivalent.
Procedure
1. Standardization of equipment—Proceed with the normal standardization using both indium and n-decane as reference standards. Follow instrument manual for adjustment to lock onto these two reference points and flatten the baseline slope as much as possible when empty pans are analyzed. Analyze the secondary standard (methyl stearate), Weigh 5 mg of the standard into the same kind of pan which will be used for the test portion (if hermetically sealed, it may be reused at a later date). Use the method sequence in Procedure, 2-7 to obtain the melting point onset (because of the high purity, only a 2 min hold is necessary for the standard after crystallization). Be certain that the heating rate during the definitive heating pattern is at 5° C./min. The melting point onset should be within ±2.00° C. of 36.5° C. If not, recheck calibration.
Note—be certain to use identical capsules for the test portion as those used for reference standards and the instrument blank reference.
2. Melt each test portion completely and weigh 7±0.200 mg of each test portion into the same kind of capsule used for the blank and reference samples (aluminum) and seal to minimize oxidation and other changes.
3. Place capsules in DSC at room temperature.
4. Heat rapidly to 80° C. and hold for 10 min.
5. Cool to −60° C. at 10° C./ml and hold for 30 min.
6. Heat to 80° C. at 5° C./min.
7. Use the baseline obtained for an empty capsule analysis from the final melt segment of the program to define the position of the baseline under the sample peaks. Overlay the final melting curve of the test portion over the curve for the empty capsule with a flexible ruler or other curve guide to define the baseline of the test portion back to where it intersects the initial deviation of the melting curve from its baseline. The baseline beneath the test portion should be a continuation of the baseline where there are no sample components present. If a shift has occurred in the heat capacity of the test portion after the melt, it will be evident relative to the baseline of the empty capsule. Have the instrument calculate the sigmoid baseline if it can, or connect the end of the peak point with the last point in which the test portion was in conjunction with the baseline of the empty capsule.
Results
Determine the onset temperature in ° C., which, if not computer generated, is an extrapolation to baseline of the steepest slope of the principal peak.

Franz Cell Method

Principle and Scope:
This method is applicable for using Franz cell apparatus for the in-vitro assessment of penetration of thioglycolic acid (TGA) and its salts through a skin mimic after the application of a depilatory composition following pre-treatment with a hydrophobic protective composition.
Penetrated TGA is quantified using Reverse Phase High Performance (or Pressure) Liquid Chromatography (RP-HPLC) with external standard quantitation at 240 nm.
Method
Reference is made to FIG. 2 and to the reference numerals therein:
1. Prepare the Vitro-Skin (IMS Vitro-Skin®, Catalogue number: P&G1013, made by IMS Inc., Portland, Me., USA) samples by cutting 8×6.2 cm segments and placing them textured side up on the racks into a hydration chamber (manufactured & sold by IMS) containing a 14.7% glycerol solution. The hydration chamber should be sealed and the vitro-skin left to hydrate at room temperature and a humidity of 80.4%±3.5% for 24 hours.
2. Prepare the receptor solution for the Franz-cell by mixing 1.90 ml formic acid (98% wt+ Fluka, by Sigma Aldrich, or equivalent), 30 ml acetonitrile (RP-HPLC grade) and 968.1 ml water (RP-HPLC grade). Set up the static Franz cell (Permegear or equivalent, 15 mm diameter unjacketed cell with a 12 ml receptor volume) by clamping it in place over suitable stirrer plates (not shown) and add a small stirrer bar (6) to each cell, fill the receptor cell (2) to the brim with the required amount of receptor solution.
3. Once hydrated, remove a sheet of vitro-skin from the hydration chamber and lay textured side up on a clean flat surface then dose 100 μl (~2 mg/cm$^2$) of hydrophobic protective composition (not shown) onto the vitro-skin and spread evenly over the surface by rubbing for 30 seconds with a gloved finger.
4. Using a scalpel blade cut the vitro-skin segment (3) into two equal sections, each large enough to completely cover the top of the cell. Place the relevant size o-ring (5) (22 mm, for the specified Franz-cell) onto each section of the vitro skin and dose to 150 mg/cm$^2$ of depilatory composition (4) ("Veet Normal Skin Hair Removal Cream" or an equivalent (an equivalent being a composition comprising 3.7% wt thioglycolic acid)) into the centre then, using a glass rod, evenly spread the cream around the inside of the o-ring (5). Using tweezers pick up the vitro-skin segment and place the vitro-skin segment, depilatory and o-ring centrally over the receptor cell (2), place donor cell (1) over the top and clamp in place. Turn on stirrer plate and start 10 minute countdown timer. After 10 minutes; turn off stirrer and remove the clamp, donor cell (1) and vitro-skin segment and place the receptor solution in a suitable container for analysis.
5. A reference sample should also be run without hydrophobic protective composition treatment on the vitro-skin. Remove a sheet of vitro-skin from the hydration chamber and lay textured side up on a clean flat surface. Repeat step 4 of the protocol to produce the reference sample.

Sample Analysis

For RP-HPLC analysis, prepare a 50 mM Formic acid (98%+Fluka) solution and mix 970 ml of this solution with 30 ml acetonitrile (HPLC grade) to act as a mobile phase during the analysis.

A reference standard solution should be made with a concentration of Calcium Thioglycolate Trihydrate of 0.94 mg/ml.

Install a Waters Atlantis T3 3 μm 4.6×50 mm column into the HPLC (although any silica-based $C_{18}$ reversed phase RP-HPLC column may be used), and ensure all solvent lines for the RP-HPLC are primed and free of leaks. Allow the mobile phase to circulate through the system for 25 minutes at 0.7 mL/Min in order to equilibrate the column Detection of the thioglycolic acid is via UV spectroscopy.

The RP-HPLC conditions are as follows:
Injection volume: 20 μL
Mobile phase flow rate: 0.70 ml/min
Run time: 10 minutes
UV Detection wavelength: 240 nm
Column temperature: 35° C.
UV sampling rate: ≥5 per second
Retention time: Thioglycolic Acid~2.5 min Calculations:
Calculate the concentration of Thioglycolic Acid in the sample $$\text{concentration (mg/ml)} = \frac{\text{weight of } std \text{ (mg)} \times \text{purity}}{25} \times \frac{3}{25}$$

Calculate the concentration of thioglycolic acid in the sample using the following formula:

concentration (mg/ml)=$A/B \times C \times E/F$

Where,
A=Peak Area of Thioglycolic Acid Sample
B=Average Peak Area of Thioglycolic Acid Standard
C=Thioglycolic Acid final STD concentration in mg/ml (0.94 mg/ml)
E=Molecular weight of Thioglycolic acid (92.12 g/mol)
F=Molecular weight of Calcium thioglycolate (184.23 g/mol)

The efficacy of the barrier (resistance to TGA penetration) can be calculated as a percentage decrease in TGA in the receptor solution:

$$\text{\% reduction} = \frac{\text{concentration without barrier} - \text{concentration with barrier}}{\text{concentration without barrier}} \times 100$$

For example, if TGA in solution without hydrophobic protective composition=75 μg/ml and TGA in solution with barrier=15 μg/ml $$\text{\% reduction} = \frac{75-60}{75} \times 100 = 85\%$$

A reduction of TGA penetration of 45% or more is believed to correlate to a significant and user-noticeable reduction in irritation.

EXAMPLES

The following compositions were made by heating all elements of the composition to the melting temperature of the highest melting point material and then mixing until a homogenous mixture was obtained. The compositions were then tested using the Franz Cell method defined above.

| Example | Composition | % Reduction in Thioglycolic Acid Penetration According to the Franz Cell Method |
|---|---|---|
| Inventive Example 1 | 6% beeswax 6% ozokerite 88% mineral oil | 99.0 |
| Inventive Example 2 | 12% beeswax 88% DC245 (Dow Corning) | 95.0 |
| Inventive Example 3 | 6% beeswax 94% mineral oil | 95.3 |
| Inventive Example 4 | 6% beeswax 94% coconut oil | 85.9 |
| Inventive Example 5 | 12% beeswax 88% DC200 | 94.1 |
| Inventive Example 6 | 2% mineral oil 98% shea butter | 86.3 |
| Inventive Example 7 | 25% olive oil 75% cocoa butter | 95.1 |
| Comparative Example 1 | 100% mineral oil | 25.0 |
| Comparative Example 2 | 100% Sunflower Seed oil | 10.8 |
| Comparative Example 3 | 100% olive oil | 0.0 |
| Comparative Example 4 | 12% shea butter 88% mineral oil | 20.1 |
| Comparative Example 5 | 12% cocoa butter 88% mineral oil | 21.1 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of removing hair from skin comprising the steps of:
   (a) applying a hydrophobic protective composition to an area of skin on which unwanted hair is growing, the hydrophobic protective composition being capable of reducing the penetration of thioglycolic acid by at least about 45%, as measured using the Franz Cell Method;
   (b) applying a depilatory composition to the area of skin to which the hydrophobic protective composition has been applied, the depilatory composition comprising a keratin reducing agent; and,
   wherein the hydrophobic protective composition comprises a homogenous mixture of triglyceride and from about 0.5% to about 3% wax by weight of the hydrophobic protective composition, wherein the weight ratio of wax:
   triglyceride is about 1:8 to about 1:25.

2. The method of claim 1, wherein the amount of hydrophobic protective composition applied to the skin is from about 0.3- about 2 mg/cm$^2$.

3. The method of claim 1, wherein the depilatory composition is applied as a layer to the skin which has been pretreated with hydrophobic protective composition, wherein the layer has a thickness from about 0.1 mm to about 5 mm.

4. The method of claim 1, comprising the following additional step between step (a) and step (b):
   (a1) massaging the hydrophobic protective composition into the skin for at least about 10 seconds.

5. The method of claim 1, comprising the following additional step immediately following step (b):
   (c) leaving the depilatory composition in place on the hydrophobic protective composition for a period of at least about 1 minute.

6. The method of claim 5, comprising the following additional step immediately following step (c):
   (d) removing both the hydrophobic protective composition and the depilatory composition from the skin by scraping, wiping or rubbing it off.

7. The method of claim 1, wherein the hydrophobic protective composition comprises from about 20% to about 99% of triglyceride by weight of the hydrophobic protective composition.

8. The method of claim 1, wherein the hydrophobic protective composition comprises from about 75% to about 99% of triglyceride by weight of the hydrophobic protective composition.

* * * * *